(12) United States Patent
Nycz (10) Patent No.: US 8,915,866 B2
(45) Date of Patent: Dec. 23, 2014

(54) IMPLANTABLE SENSOR AND ASSOCIATED METHODS

(75) Inventor: Jeffrey H. Nycz, Collierville, TN (US)

(73) Assignee: Warsaw Orthopedic, Inc., Warsaw (IN)

( * ) Notice: Subject to any disclaimer, the term of this patent is extended or adjusted under 35 U.S.C. 154(b) by 1551 days.

(21) Appl. No.: 12/016,421

(22) Filed: Jan. 18, 2008

(65) Prior Publication Data

US 2009/0187120 A1    Jul. 23, 2009

(51) Int. Cl.
| | |
|---|---|
| A61B 7/00 | (2006.01) |
| A61B 5/103 | (2006.01) |
| A61B 5/117 | (2006.01) |
| A61B 5/00 | (2006.01) |
| A61B 5/07 | (2006.01) |
| A61B 5/107 | (2006.01) |
| A61B 19/00 | (2006.01) |

(52) U.S. Cl.
CPC .............. *A61B 5/4514* (2013.01); *A61B 5/076* (2013.01); *A61B 5/107* (2013.01); *A61B 5/4528* (2013.01); *A61B 2019/5408* (2013.01); *A61B 2019/5416* (2013.01); *A61B 2019/5458* (2013.01); *A61B 2562/0219* (2013.01); *A61B 5/686* (2013.01); *A61B 5/6878* (2013.01)
USPC ............................. 600/586; 600/587; 600/595

(58) Field of Classification Search
CPC ..... A61B 5/0031; A61B 5/076; A61B 5/4528
USPC .......................................... 600/586, 587, 595
See application file for complete search history.

(56) References Cited

U.S. PATENT DOCUMENTS

| | | | |
|---|---|---|---|
| 4,214,322 A | 7/1980 | Kraus | |
| 4,602,538 A | 7/1986 | Neuhaus | |
| 4,793,825 A | 12/1988 | Benjamin et al. | |
| 4,813,435 A | 3/1989 | Arms | |
| 4,967,764 A | 11/1990 | Basser | |
| 4,993,428 A | 2/1991 | Arms | |
| 5,016,631 A | 5/1991 | Hogrefe | |

(Continued)

FOREIGN PATENT DOCUMENTS

EP    1442715 B1    7/2007

OTHER PUBLICATIONS

Lanyon, L.E., Paul, I.L., Rubin, C.T., Thrasher, E.L., DeLaura, R., Rose, R.M., and Radin, E.L., "In Vivo Strain Measurements from Bone and Prosthesis following Total Hip Replacement", The Journal of Bone and Joint Surgery, vol. 63-A, No. 6, pp. 989-1000, 1981.

(Continued)

*Primary Examiner* — Adam Eiseman (74) *Attorney, Agent, or Firm* — Sorell Lenna & Schmidt LLP (57) ABSTRACT

Implantable sensors and methods for detecting changes in a characteristic of a soft tissue is disclosed. In one embodiment, an implantable sensor for detecting indicators of cartilage wear in a joint is provided. The implantable sensor includes a sensing element for detecting a signal indicative of a characteristic of the cartilage of the joint and a telemetry circuit in communication with the sensing element for transmitting a data set representative of the detected signal. In another embodiment, a system for detecting changes in joint cartilage includes an implantable acoustic sensing element and an external receiver in communication with the implantable acoustic sensing element. In other embodiments, methods of detecting cartilage degradation in a joint and methods of using the disclosed sensors are provided.

15 Claims, 7 Drawing Sheets

(56) References Cited

U.S. PATENT DOCUMENTS

| | | |
|---|---|---|
| 5,030,236 A | 7/1991 | Dean |
| 5,083,573 A | 1/1992 | Arms |
| 5,125,408 A | 6/1992 | Basser |
| 5,197,488 A | 3/1993 | Kovacevic |
| 5,292,342 A | 3/1994 | Nelson et al. |
| 5,353,800 A | 10/1994 | Pohndorf et al. |
| 5,360,016 A | 11/1994 | Kovacevic |
| 5,374,285 A | 12/1994 | Vaiani et al. |
| 5,391,250 A | 2/1995 | Cheney, II et al. |
| 5,413,116 A * | 5/1995 | Radke et al. ............... 600/590 |
| 5,425,775 A | 6/1995 | Kovacevic et al. |
| 5,438,990 A | 8/1995 | Wahlstrand et al. |
| 5,456,724 A | 10/1995 | Yen et al. |
| 5,470,354 A | 11/1995 | Hershberger et al. |
| 5,497,147 A | 3/1996 | Arms et al. |
| 5,533,519 A * | 7/1996 | Radke et al. ............... 600/595 |
| 5,535,752 A | 7/1996 | Halperin et al. |
| 5,549,654 A | 8/1996 | Powell |
| 5,564,434 A | 10/1996 | Halperin et al. |
| 5,586,553 A | 12/1996 | Halili et al. |
| 5,593,431 A | 1/1997 | Sheldon |
| 5,695,496 A | 12/1997 | Orsak et al. |
| 5,701,895 A | 12/1997 | Prutchi et al. |
| 5,777,467 A | 7/1998 | Arms et al. |
| 5,792,076 A | 8/1998 | Orsak et al. |
| 5,814,089 A | 9/1998 | Stokes et al. |
| 5,833,603 A | 11/1998 | Kovacs et al. |
| 5,891,180 A | 4/1999 | Greeninger et al. |
| 5,914,593 A | 6/1999 | Arms et al. |
| 5,935,171 A | 8/1999 | Schneider et al. |
| 5,944,745 A | 8/1999 | Rueter |
| 6,034,296 A | 3/2000 | Elvin et al. |
| 6,044,297 A | 3/2000 | Sheldon et al. |
| 6,045,513 A | 4/2000 | Stone et al. |
| 6,059,784 A | 5/2000 | Perusek |
| 6,083,248 A | 7/2000 | Thompson |
| 6,091,986 A | 7/2000 | Keimel |
| 6,102,874 A | 8/2000 | Stone et al. |
| 6,120,502 A | 9/2000 | Michelson |
| 6,120,540 A | 9/2000 | Apple et al. |
| 6,143,035 A | 11/2000 | McDowell |
| 6,152,885 A | 11/2000 | Taepke |
| 6,155,267 A | 12/2000 | Nelson |
| 6,164,284 A | 12/2000 | Schulman et al. |
| 6,185,452 B1 | 2/2001 | Schulman et al. |
| 6,245,109 B1 | 6/2001 | Mendes et al. |
| 6,280,409 B1 | 8/2001 | Stone et al. |
| 6,292,680 B1 | 9/2001 | Somogyi et al. |
| 6,317,625 B1 | 11/2001 | Olson et al. |
| 6,319,241 B1 | 11/2001 | King et al. |
| 6,330,885 B1 | 12/2001 | Weissman et al. |
| 6,368,274 B1 | 4/2002 | Van Antwerp et al. |
| 6,398,710 B1 | 6/2002 | Ishikawa et al. |
| 6,415,184 B1 | 7/2002 | Ishikawa et al. |
| 6,432,050 B1 | 8/2002 | Porat et al. |
| 6,434,045 B2 | 8/2002 | Mihnea et al. |
| 6,447,448 B1 | 9/2002 | Ishikawa et al. |
| 6,449,508 B1 | 9/2002 | Sheldon et al. |
| 6,475,170 B1 | 11/2002 | Doron et al. |
| 6,477,424 B1 | 11/2002 | Thompson et al. |
| 6,478,824 B1 | 11/2002 | Hagenmeyer |
| 6,480,744 B2 | 11/2002 | Ferek-Petric |
| 6,486,588 B2 | 11/2002 | Doron et al. |
| 6,529,127 B2 | 3/2003 | Townsend et al. |
| 6,564,807 B1 | 5/2003 | Schulman et al. |
| 6,572,543 B1 * | 6/2003 | Christopherson et al. .... 600/300 |
| 6,573,706 B2 | 6/2003 | Mendes et al. |
| 6,583,630 B2 | 6/2003 | Mendes et al. |
| 6,605,039 B2 | 8/2003 | Houben et al. |
| 6,605,089 B1 | 8/2003 | Michelson |
| 6,610,096 B2 | 8/2003 | MacDonald |
| 6,628,989 B1 | 9/2003 | Penner et al. |
| 6,656,117 B2 | 12/2003 | Jentsch et al. |
| 6,656,135 B2 | 12/2003 | Zogbi et al. |
| 6,666,821 B2 | 12/2003 | Keimel |
| 6,671,550 B2 | 12/2003 | Iaizzo et al. |
| 6,681,135 B1 | 1/2004 | Davis et al. |
| 6,699,200 B2 | 3/2004 | Cao et al. |
| 6,706,005 B2 | 3/2004 | Roy et al. |
| 6,706,071 B1 | 3/2004 | Wolter |
| 6,731,976 B2 | 5/2004 | Penn et al. |
| 6,738,671 B2 | 5/2004 | Christophersom et al. |
| 6,761,741 B2 | 7/2004 | Iesaka |
| 6,764,446 B2 | 7/2004 | Wolinsky et al. |
| 6,807,439 B2 | 10/2004 | Edwards et al. |
| 6,809,653 B1 | 10/2004 | Mann et al. |
| 6,810,753 B2 | 11/2004 | Valdevit et al. |
| 6,821,299 B2 | 11/2004 | Kirking et al. |
| 6,885,891 B2 | 4/2005 | Cho et al. |
| 7,001,346 B2 | 2/2006 | White |
| 7,001,393 B2 | 2/2006 | Schwenke et al. |
| 7,024,248 B2 | 4/2006 | Penner et al. |
| 7,097,662 B2 * | 8/2006 | Evans et al. ............... 623/18.11 |
| 7,114,502 B2 | 10/2006 | Schulman et al. |
| 7,179,295 B2 | 2/2007 | Kovacevic |
| 7,195,645 B2 | 3/2007 | Disilvestro et al. |
| 7,328,131 B2 | 2/2008 | Donofrio et al. |
| 8,486,070 B2 * | 7/2013 | Morgan et al. ............... 606/62 |
| 2002/0024450 A1 | 2/2002 | Townsend et al. |
| 2002/0049478 A1 * | 4/2002 | Ding et al. ............... 607/17 |
| 2002/0133094 A1 * | 9/2002 | Wilcox et al. ............... 600/587 |
| 2002/0177790 A1 | 11/2002 | Meredith et al. |
| 2003/0069644 A1 | 4/2003 | Kovacevic et al. |
| 2003/0120150 A1 | 6/2003 | Govari |
| 2003/0139690 A1 | 7/2003 | Aebli et al. |
| 2004/0011137 A1 | 1/2004 | Hnat et al. |
| 2004/0019382 A1 | 1/2004 | Amirouche et al. |
| 2004/0068205 A1 | 4/2004 | Zogbi et al. |
| 2004/0087869 A1 * | 5/2004 | Treppo et al. ............... 600/547 |
| 2004/0129095 A1 | 7/2004 | Churchill et al. |
| 2004/0133079 A1 * | 7/2004 | Mazar et al. ............... 600/300 |
| 2004/0152972 A1 | 8/2004 | Hunter |
| 2004/0186396 A1 | 9/2004 | Roy et al. |
| 2004/0204647 A1 | 10/2004 | Grupp et al. |
| 2004/0204744 A1 | 10/2004 | Penner et al. |
| 2004/0243207 A1 | 12/2004 | Olson et al. |
| 2005/0010299 A1 | 1/2005 | Disilvestro |
| 2005/0010300 A1 | 1/2005 | Disilvestro et al. |
| 2005/0010302 A1 | 1/2005 | Dietz et al. |
| 2005/0012610 A1 | 1/2005 | Liao et al. |
| 2005/0027192 A1 | 2/2005 | Govari et al. |
| 2005/0099290 A1 | 5/2005 | Govari |
| 2005/0165317 A1 | 7/2005 | Turner et al. |
| 2005/0234555 A1 | 10/2005 | Sutton et al. |
| 2006/0004431 A1 | 1/2006 | Fuller et al. |
| 2006/0032314 A1 | 2/2006 | Hnat et al. |
| 2006/0036246 A1 | 2/2006 | Carl et al. |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0052782 A1 | 3/2006 | Morgan et al. |
| 2006/0069436 A1 | 3/2006 | Sutton et al. |
| 2006/0069447 A1 | 3/2006 | DiSilvestro et al. |
| 2006/0100508 A1 | 5/2006 | Morrison |
| 2006/0224088 A1 | 10/2006 | Roche |
| 2006/0229534 A1 | 10/2006 | Chang et al. |
| 2006/0247773 A1 | 11/2006 | Stamp |
| 2006/0271199 A1 | 11/2006 | Johnson |
| 2007/0005145 A1 | 1/2007 | Banks et al. |
| 2007/0179568 A1 | 8/2007 | Nycz et al. |
| 2007/0179739 A1 * | 8/2007 | Donofrio et al. ............... 702/160 |
| 2007/0238992 A1 * | 10/2007 | Donofrio et al. ............... 600/437 |

OTHER PUBLICATIONS

Hodge, W.A., Fijan, R.S., Carlson, K.L., Burgess, R.G., Harris, W.H., and Mann, R.W., "Contact Pressures in the Human Hip Joint Measured In Vivo", Proc. of National Academy of Science, U.S.A., No. 83, pp. 28779-2883, 1986.

Davy, D.T., Kotzar, G.M., Brown, R.H., Heiple, K.G.Sr., Goldberg, V.M., Heiple K.G.Jr., Berilla, J., and Burstein, A.H., "Telemetric Force Measurements across the Hip after Total Arthro-plasty", Journal of Bone and Joint Surgery, vol. 70-A, No. 1, Jan. 1988.

(56) References Cited

OTHER PUBLICATIONS

F. Graichen, G. Bergmann, A. Rohlmann, Patient Monitoring System for Load Measurement with Spinal Fixation Devices, Med. Eng. Phys. 18, [1996], 167-174.

F. Kummer, T. Lyon, J. Zuckerman, Development of Telemeterized Shoulder Prosthesis, Clinical Orthopaedics & Related Research. (330):31-34, Sep. 1996.

Friedmar Graichen, Georg Bergmann, Antonius Rohlmann, Hip Endoprosthesis for In Vivo Measurement of Joint Force and Temperature, Journal of Biomechanics 32 [1999] 1113-1117.

D. D'Lima, J. Slamin, B. Morris, "An implantable telemetry system to measure intra-articular tibial forces", Orthopedic Research Society, Anaheim, CA 1999.

Burny F, Donkerwolcke M, Moulart F, Bourgois R, Puers R, Van Schuylenbergh K, Barbosa M, Paiva O, Rodes F, Begueret JB, Lawes P., Concept, design and fabrication of smart orthopedic implants., Med Eng Phys. Sep. 2000;22 (7):469-79.

F. Graichen, A. Rohlmann, G. Bergmann, In vivo Load Measurements With Instrumented Orthopaedic Implants, 17th Int. Symposium on Biotelemetry, Brisbane, Australia 2003.

Ledet EH, Tymeson MP, DiRisio DJ, Cohen B, Uhl RL., Direct real-time measurement of in vivo forces in the lumbar spine., Spine J. Jan.-Feb. 2005;5(1):85-94.

D'Lima DD, Townsend CP, Arms SW, Morris BA, Colwell CW Jr., An implantable telemetry device to measure intra-articular tibial forces., J Biomech. Feb. 2005;38(2):299-304.

Jaecques, S.V.N., Pastrav, C., Zahariuc, A., Van der Perre, G., Analysis of the Fixation Quality of Cementless Hip Prostheses Using a Vibrational Technique, K.U. Leuve, Department of Mechanical Engineering, Div. of Biomechanics and Engineering Design, 200A, B-3001.

Graichen, F., Bergmann, G., Rohlmann, A., Implantable Telemetry System for Measurement of Hip Joint Force and Temperature., Biomechanics-Laboratory, Oskar-Helene-Heim, Orthopaedic Hospital of the Free University of Berlin, Clayallee 229, D-14195 Berlin German.

* cited by examiner

IMPLANTABLE SENSOR AND ASSOCIATED METHODS

FIELD/BACKGROUND

The present disclosure is directed to improved instrumentation and methods for measuring and monitoring soft tissue. More particularly, in one aspect the present disclosure is directed to an implantable sensor for detecting changes in soft tissue of a joint.

The present disclosure relates to the assessment of soft tissue. The disclosure may have particularly useful application in the assessment of soft tissues as it relates to joints and monitoring the need for medical treatment, including surgical procedures. In some aspects, the surgical procedure is a total joint replacement surgery, such as the implantation of a hip, knee, shoulder, ankle, spinal, or wrist prosthesis. The disclosure may also have particularly useful application in the assessment of soft tissue as it relates to soft tissue repairs such as ACL reconstruction, meniscal reconstruction, and other soft tissue repairs, for example.

Joint prostheses are usually manufactured of durable materials such as metals, ceramics, or hard plastics and are affixed to articulating ends of the bones of the joint. Joint prostheses usually include an articulating surface composed of a material designed to minimize the friction between the components of the joint prostheses. For example, in a hip prosthesis the femoral component is comprised of a head (or ball) and a stem attached to the femur. The acetabular component is comprised of a cup (or socket) attached to the acetabulum and most often includes a polyethylene articulating surface. The ball-in-socket motion between the femoral head and the acetabular cup simulates the natural motion of the hip joint and the polyethylene surface helps to minimize friction during articulation of the ball and socket.

As described, total joint replacements often require components to articulate against polyethylene or metal bearing surfaces. This articulation has been shown to release submicron particle wear debris, often polyethylene wear debris. This debris can lead to osteolytic lesions, implant loosing, and possibly the need for revision surgery. Early detection of particle wear debris or the onset of osteolytic lesions allows an orthopedic surgeon to treat the potential problem before it escalates to the point of causing severe medical harm to the patient and/or the need for revision surgery.

Further, in soft tissue repairs, such as ACL reconstruction, the tissue may have problems with graft incorporation and/or failure to fully heal the defect. Tracking the healing process and tissue integrity in soft tissue repairs can assist the surgeon in determining the appropriate postoperative treatments and physical therapy. Also, early detection of a potential problem provides the surgeon with the potential ability to treat the affected tissue before the problem becomes more serious or requires revision surgery.

Therefore, there remains a need for improved instrumentation and methods for monitoring soft tissue and, in particular, the soft tissue of joints.

SUMMARY

The present disclosure provides implantable sensors and methods for detecting signals indicative of tissue characteristics and, in particular, tissue degradation or wear.

In one aspect, the present disclosure provides an implantable sensor for detecting indicators of soft tissue wear of a joint. The implantable sensor includes a sensing element having an external surface for engaging a portion of a bone adjacent the joint. The external surface is shaped or otherwise configured to maintain the sensing element in a fixed position within the bone. The sensing element is for detecting a signal indicative of a characteristic of the soft tissue of the joint. The implantable sensor also includes a telemetry circuit in communication with the sensing element. The telemetry circuit is adapted for transmitting a data set representative of the detected signal outside of the bone.

In another aspect, the present disclosure provides a system for detecting changes in joint cartilage. The system includes an implantable acoustic sensor for detecting an acoustic signal indicative of a characteristic of the joint cartilage. The sensor is adapted to communicate a data set representative of the detected signal to an external receiver. The sensor is also suitable for injection into a tissue adjacent the joint. The system also includes an external receiver in communication with the sensor. The external receiver is configured for receiving the data set representative of the detected signal from the sensor.

In another aspect, the present disclosure provides a method for detecting soft tissue degradation in a joint. The method includes providing at least one acoustic sensor for detecting a signal indicative of a characteristic of the soft tissue of a joint, where the at least one sensor has an external surface configured for implantation within a bone. The method includes implanting the at least one sensor into a bone adjacent the joint; operating the at least one sensor to detect a reference signal indicative of the characteristic of the soft tissue; and operating the at least one sensor to detect a subsequent signal indicative of the characteristic of the soft tissue. Finally, the method compares the subsequent signal to the reference signal to detect any changes in the characteristic of the soft tissue.

In another aspect, the present disclosure provides a method that includes providing a plurality of implantable sensors for detecting signals indicative of a characteristic of cartilage of a joint and implanting each of the plurality of sensors into a bone adjacent the joint. The method also includes operating the plurality of sensors to detect a reference signal indicative of the characteristic of the cartilage and operating the plurality of sensors to detect a subsequent signal indicative of the characteristic of the cartilage. The method compares the subsequent signal to the reference signal to detect any changes in the characteristic of the cartilage.

Further aspects, forms, embodiments, objects, features, benefits, and advantages of the present disclosure shall become apparent from the detailed drawings and descriptions provided herein.

DESCRIPTION OF THE PREFERRED EMBODIMENTS

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications in the described devices, instruments, methods, and any further application of the principles of the disclosure as described herein are contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure.

Figure 1:
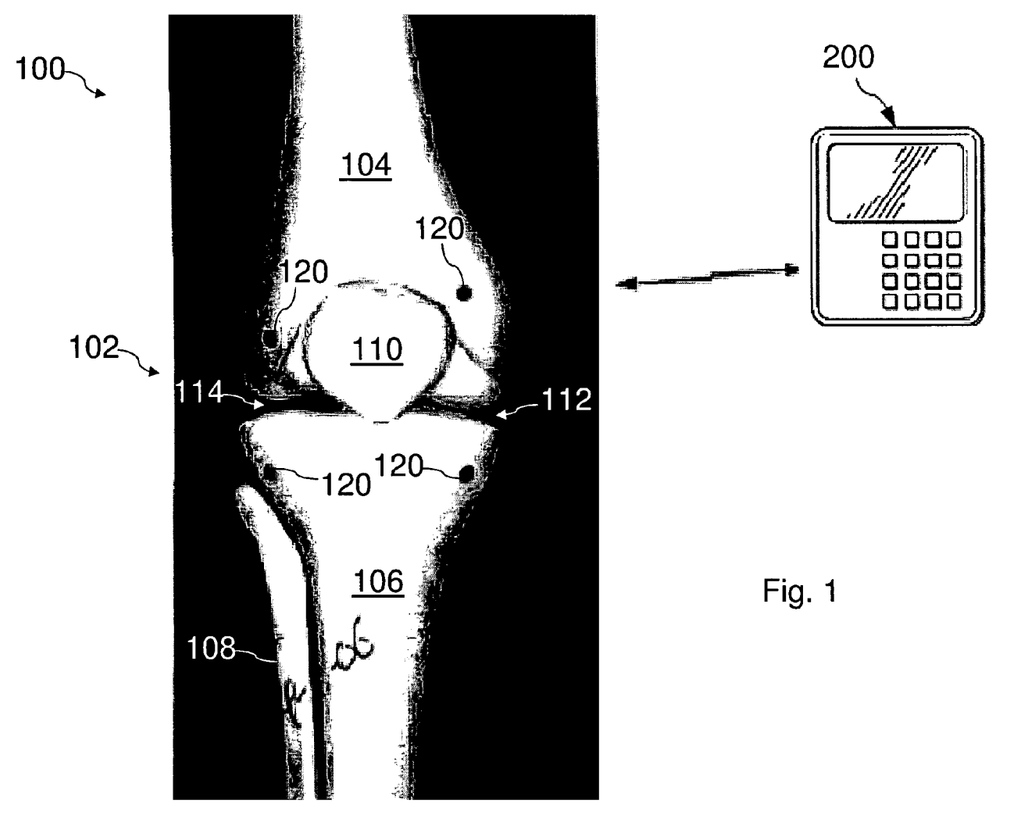
FIG. 1 is a partial front view of a system for monitoring the soft tissue of a joint in use with a knee joint according to one embodiment of the present disclosure.

Referring now to FIG. 1, shown therein is a system 100 for monitoring changes of a characteristic in the soft tissue of a joint according to one aspect of the present disclosure. The system 100 is shown in use with a knee joint 102. The knee joint 102 includes a plurality of bones, ligaments, tendons, cartilage, and menisci. As shown in FIG. 1, the knee joint 102 comprises a femur 104, a tibia 106, a fibula 108, and a patella 110. The knee joint 102 also includes articular cartilage and menisci (not specifically illustrated) positioned between the femur 104 and the tibia 106. In that regard, the knee joint 102 includes a medial portion 112 comprised of a medial section of the articular cartilage and the medial meniscus. The knee joint 102 also includes a lateral portion 114 comprised of a lateral section of the articular cartilage and the lateral meniscus.

Figure 2:
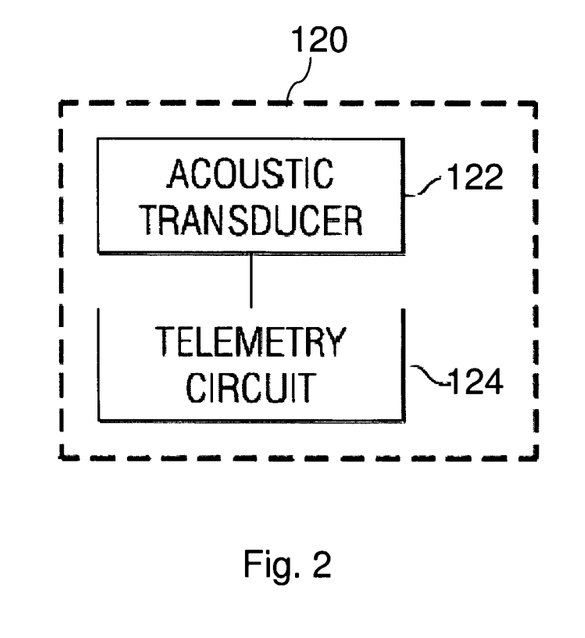
FIG. 2 is a schematic illustration of a sensor of the system of FIG. 1.

In the current embodiment, the system 100 is configured to monitor changes in the medial and lateral portions 112 and 114 of the articular cartilage and menisci. The system 100 includes a plurality of sensors 120 and an external device 200. Referring now to FIG. 2, shown therein is a schematic view of a sensor 120 according to one embodiment of the present disclosure. Each sensor 120 includes an acoustic transducer 122 and a telemetry circuit 124. The acoustic transducer 122 is adapted for detecting acoustic signals indicative of a characteristic of a soft tissue. The telemetry circuit 124 is adapted for providing power to the acoustic transducer 122 and communicating with an external device 200. It is contemplated that the telemetry circuit 124 will provide power to the acoustic transducer 122 via inductive coupling or other known means of passive power supply. It is also contemplated that the external device 200 may be utilized to provide the power to the sensor 120 through coupling. That is, the sensor 120 may be externally powered by the external device 200. Powering the sensor 120 externally allows the sensor 120 to remain in a dormant state whenever an external power supply is not available and then become active when the external power supply is present. In this manner, the sensor 120 does not require a dedicated power supply such as a battery. This allows the sensor 120 to be much smaller than would otherwise be possible with a dedicated power supply, which allows placement of the sensor 120 in more locations without interfering with body mechanics or functions.

Referring to FIGS. 1 and 2, the sensors 120 are configured to detect and/or monitor changes in the medial and lateral portions 112 and 114 of the articular cartilage and menisci. In that regard, in the current embodiment the sensors 120 are acoustic sensors. Therefore, the sensors 120 are configured to detect acoustic signals emitted by the knee joint 102 and, in particular, the articular cartilage and menisci. In that regard, acoustic signals are intended to include both audible sounds and vibrations created by the knee joint 102. For example, in one embodiment, the sensors 120 listen to the sounds created by the articular cartilage and meniscus during natural motion of the knee joint 102. In a healthy knee joint, the articular cartilage and menisci typically provide for a smooth motion and a smooth sound is associated therewith. However, as the articular cartilage and/or menisci begin to degrade, the motion becomes rougher and a more jagged sound is associated with the motion. Similarly, in a healthy knee joint with smooth motion, the vibrations caused by movement of the knee are minimal. However, as the articular cartilage and/or menisci begin to degrade and the motion becomes rougher, a more pronounced vibration is associated with the motion. Thus, by detecting the changes in the acoustic signals (sounds and/or vibrations) emitted during motion of the knee joint 102, changes in the articular cartilage and menisci can be detected.

In some embodiments, the sensors 120 establish a baseline or reference signal for the individual patient and then compare subsequent acoustic signals to the reference signal. Detected changes in the subsequent acoustic signals relative to the reference signal can be analyzed to determine if the change is indicative of soft tissue degradation, soft tissue healing, or other changes in the soft tissue. Thus, in one aspect of the current embodiment, changes in the detected acoustic signal could indicate that the medial and/or lateral portions 112 and 114 of the articular cartilage and menisci are degrading. The magnitude of difference between the acoustic signals may be correlated to the degree of degradation, such that a sufficient change in the acoustic signal is an indication that joint replacement surgery or other medical treatment should be considered. In other embodiments, the detected acoustic signals are compared to an established standard signal for a healthy knee joint of a similar patient rather than a reference signal from the patient's knee. The standard signal may be affected by such things as the patient's age, weight, prior medical procedures, and/or other medical conditions. In this regard, comparing the acoustic signals to that of an established standard can provide a more absolute determination of the health of the soft tissue of the knee joint, while comparing the acoustic signals to a patient-specific reference signal can provide relative information for determining whether the patient's condition is improving, getting worse, or staying the same. In some embodiments, these approaches are combined to provide a more complete analysis of the patient's condition.

In FIG. 1, the system 100 is shown having four sensors 120, two of the sensors 120 implanted into a distal portion of the femur 104 and two of the sensors 120 implanted into a proximal portion of the tibia 106. In general, it is advantageous to position the sensors 120 adjacent to or in close proximity to the soft tissue to be monitored, but without affecting the motion of the joint and/or soft tissue. Thus, in the current embodiment, two of the sensors 120 are positioned on the medial side of the knee 102—one in the femur 104 and one in the tibia 106—for monitoring the medial section of the articular cartilage and the medial meniscus, and two of the sensors 120 are positioned on the lateral side of the knee joint 102—one in the femur 104 and one in the tibia 106—for monitoring the lateral section of the articular cartilage and the lateral meniscus. In the current embodiment, each sensor 120 of the pair of sensors operates independently. For example, the medial-femoral sensor 120 operates as a stand alone sensor, providing data independent of the other sensors 120. In this manner, each of the medial sensors 120 provides a data point for the condition of the medial portion 112 and each of the lateral sensors 120 provides a data point for the condition of the lateral portion 114.

In some embodiments, by using a pair of independent sensors to monitor each of the medial and lateral portions 112 and 114, a redundancy or check is built into the system for each side. For example, in one embodiment, each sensor 120 of the pair of sensors operates to monitor overlapping portions of the medial or lateral portions 112 and 114. In one such embodiment, the medial-femoral sensor and the medial-tibial sensor are configured to monitor changes to the medial section of the articular cartilage and the medial meniscus. Thus, each of the medial-femoral and medial-tibial sensors 120 should detect similar changes in the acoustic signals for the medial section of the articular cartilage and the medial meniscus. If for some reason the medial-femoral sensor and the medial-tibial sensor detect divergent acoustic signals, then that could be an indication of a malfunction in the system 100. In other embodiments, each sensor 120 of the pair of sensors operates to monitor separate portions of the medial or lateral portions 112 and 114. For example, in one embodiment, the medial-femoral sensor is configured to monitor changes to the medial section of the articular cartilage while the medial-tibial sensor is configured to monitor changes to the medial meniscus. In this way, the medial-femoral sensor and the medial-tibial sensor operate together to monitor the medial portion 112, but each of the sensors 120 operates independently.

It is fully contemplated that the sensors 120 may work together to form a sensing network. Under such an approach, the sensors 120 may be configured to monitor changes in soft tissue and also where those changes are occurring. Utilizing a plurality of sensors 120 allows a spatial relationship to be determined based on the location of the sensors 120 and then based on the signals detected the location of any tissue density changes may be mapped accordingly. The plurality of sensors 120 may triangulate the location of the signals. In this regard, the plurality of sensors 120 may be spaced apart to allow for accurate triangulation. In one embodiment, the plurality of sensors 120 are spaced apart by at least 5 mm. In another embodiment, the sensors 120 are spaced apart by at least 20 mm.

In addition or alternatively, the plurality of sensors 120 may function as redundancies to one another. That is, rather than working together each individual sensor 120 would function independently. Then, the data obtained by each sensor 120 could be compared to the data obtained by the other sensors 120 to make a determination of changes in soft tissue. Under such an approach, the failing of a single sensor 120 would not create a need to replace the sensor 120 and therefore eliminate the need for an additional medical procedure. Further, it is fully contemplated that all of the sensors 120 of the present disclosure may be utilized independently or as part of a plurality of sensors 120.

In yet other embodiments, each pair of sensors (medial and lateral in the current embodiment) may operate together in a send-and-receive manner. For example, in some embodiments, one sensor is adapted for emitting an energy signal and the other sensor is adapted for receiving an energy signal. Energy signal in this context is intended to include acoustic signals, electromagnetic signals, magnetic signals, ultrasound, and other suitable energy signals. Continuing the example of FIG. 1, the medial-femoral sensor may be configured to emit an energy signal through the medial section of the articular cartilage and the medial meniscus towards the medial-tibial sensor. The medial-tibial sensor may be adapted to receive the energy signal. Based on the received energy signal, characteristics of the medium the energy signal passed through can be determined. In one particular embodiment, the received energy signal is used to measure the impedance of the soft tissue. Generally, a reduction in the impedance of the soft tissue is indicative of tissue degradation. This can be the result of holes forming in the soft tissue and/or a decrease in the density of the soft tissue. As described above, in some embodiments a baseline or reference point for the received energy signal can be established and any subsequently received energy signals can be compared to the baseline to detect changes in the articular cartilage and/or menisci. On the other hand, the received energy signals can be compared to an established standard signal for a healthy knee joint of a similar patient. In some embodiments, these approaches may be combined.

In other embodiments, the system 100 may include greater or fewer sensors 120. In some embodiments, the sensors 120 operate together in sensor arrays comprised of three or more sensors. In at least one embodiment, the system 100 includes a single sensor 120. In other embodiments, the sensors 120 may be positioned elsewhere around and/or within the knee joint 102. In particular, the sensors 120 may be arranged and/or positioned based on the specific type(s) of soft tissue of the knee joint 102 to be monitored. It is fully contemplated that the sensors 120 may be disposed at a plurality of locations including, but not limited to, within a bone or tissue, attached to a bone or tissue, adjacent to a bone or tissue, within or integral to an artificial implant, attached to an artificial implant, adjacent to an artificial implant, or any combination of these locations. Where the sensor 120 is adapted for being disposed at least partially within bone, it is contemplated that the sensor 120 may be shaped or coated in a substance to facilitate bone growth and incorporation of the sensor 120 into the bone. In that regard, in some embodiments, the sensor 120 is sized and shaped such that it may be injected into the bone using an injection gun and/or catheter. In some embodiments, the sensor 120 has a substantially spherical shape. In other embodiments, the sensor 120 has a substantially cylindrical shape. However, it is understood that the sensor 120 may have any shape suitable for implantation. Further, the sensor 120 may be incorporated into implantable fixation devices, such as but not limited to bone screws, nails, and staples.

FIG. 1 shows the implantable sensors 120 in wireless communication with the external device 200. In particular, the telemetry circuit 124 is adapted for communicating wirelessly with the external device 200. There are several types of wireless telemetry circuits that may be employed for communication between the implantable sensors 120 and the external device 200. For example, RFID, inductive telemetry, acoustic energy, near infrared energy, "Bluetooth," computer networks, and other wireless communication networks are all possible means of wireless communication. In some embodiments, the telemetry circuit 124 is adapted for RFID communication such that at least a portion of the telemetry circuit 124 includes a passive RFID tag. Using a passive RFID tag helps to limit the power requirements of the telemetry circuit 124 and, therefore, the implantable sensor 120 as a whole, yet still allows wireless communication to the external device 200. Through the wireless communication, the external device 200 is able to retrieve data signals representative of the acoustic signals detected by the acoustic transducer 122. In some embodiments, the external device 200 includes a processor for analyzing the acoustic signals detected by the implantable sensors 120 and determining any changes in the soft tissue. In some embodiments, the external device 200 includes an output, such as a display, speaker, tactile feedback, or other output, for communicating the raw data and/or analyzed acoustic signals in a human intelligible form.

In some embodiments, the external device 200 is a computer system or part thereof. In one particular embodiment, the external device 200 is a laptop computer. A computer system typically includes at least hardware capable of executing machine readable instructions, as well as the software for executing acts (typically machine-readable instructions) that produce a desired result. In addition, a computer system may include hybrids of hardware and software, as well as computer sub-systems. Hardware generally includes at least processor-capable platforms, such as client-machines (also known as personal computers or servers), and hand-held processing devices (such as smart phones, cell phones, personal digital assistants (PDAs), hand-held writing tablets, or personal computing devices (PCDs)). Further, hardware may include any physical device that is capable of storing machine-readable instructions, such as memory or other data storage devices. Other forms of hardware include hardware sub-systems, including transfer devices such as modems, modem cards, ports, and port cards, for example.

Software includes any machine code stored in any memory medium, such as RAM or ROM, and machine code stored on other devices (such as floppy disks, flash memory, or a CD ROM, for example). Software may include source or object code, for example. In addition, software encompasses any set of instructions capable of being executed on a computer system. It is recognized that combinations of software and hardware could also be used for providing enhanced functionality and performance for certain embodiments of the present disclosure. Accordingly, it should be understood that combinations of hardware and software are also included within the definition of a computer system and are envisioned by the present disclosure as possible equivalent structures and equivalent methods.

It is contemplated that the system 100 and sensors 120 may be utilized to detect indicators of soft tissue condition over a regular interval, such as every 6 months, monthly, weekly, daily, or otherwise as determined by a treating physician. In this regard, it is contemplated that the patient may return to the doctor's office for each reading. At such time, the doctor would place the external device 200 in the vicinity of the sensors 120. Through inductive coupling via the telemetry unit 124 the sensor 120 would be powered by the external device 200. The acoustic transducer 122 would then take a reading by detecting acoustic signals associated with motion of the knee joint 102. This reading would then be relayed to the external device 200 via the telemetry circuit 124. The reading may then be analyzed to determine any changes to the soft tissue. Appropriate medical treatment may then be taken based on the reading. It is also contemplated that the patient may obtain these readings without going to the doctor's office. For example, the patient may be provided with an external device 200 that is capable of powering the sensors 120, obtaining the readings, and then relaying the readings to the doctor's office. For example, the external device may transfer the readings to the doctors office via a telecommunications or computer network. It is contemplated that a system similar to that of Medtronic's CareLink may be utilized.

While the sensors 120 have been described as having an acoustic transducer 122 and a telemetry unit 124, it is fully contemplated that the sensors 120 may include additional components, including but not limited to a stored-energy power supply (e.g., a battery), a signal processor, a memory unit, a microcontroller, a micromotor, and/or other components. Further, it is fully contemplated that the functions of the various components of the sensor 120 may be combined or grouped into a single component or distributed among a plurality of components. Sensors 120 that include one or more of the additional components listed above may have enhanced functionality and/or may function in a variety of ways.

Figure 3:
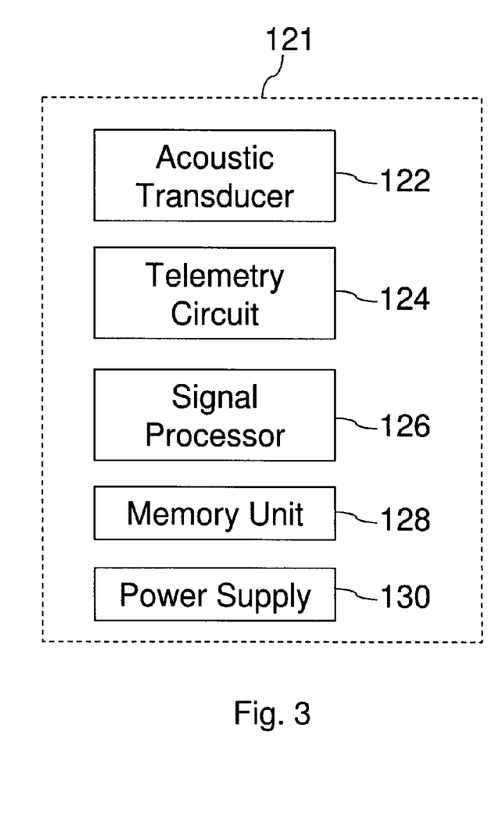
FIG. 3 is a schematic illustration of a sensor according to another embodiment of the present disclosure.

Referring to FIG. 3, shown therein is a sensor 121 according to one embodiment of the present disclosure. The sensor 121 includes an acoustic transducer 122, a telemetry circuit 124, a signal processor 126, and a memory unit 128, and a power supply 130. The memory unit 128 is configured to store data it receives from the signal processor 126. It is fully contemplated that the memory unit 128 may utilize known compression algorithms and functions to save on memory and size requirements. In this regard, it is also contemplated that the memory unit 128 may store additional data with respect to each signal such as a timestamp, the specific characteristics of the signal, or any other relevant data. In this respect, the signal processor 126 and memory 128 may be configured to keep the various types of data the orthopedic surgeon or treating physician would like to have to monitor the soft tissue. In that regard, the treating physician may select the types and/or amounts of data to be obtained and stored by the sensor 121.

Supplying the power requirements of the implantable sensor 121 is a power source 130. In some embodiments, the power source 130 is a battery. In this manner, the sensor 121 may be internally powered. The battery may be a lithium iodine battery similar to those used for other medical implant devices such as pacemakers. However, it is understood that the battery may be any type of battery suitable for implantation. It is fully contemplated that the battery may be rechargeable. It is also contemplated that the battery may be recharged by an external device so as to avoid the necessity of a surgical procedure to recharge the battery. For example, in one embodiment, the battery is rechargeable via inductive coupling.

It is also contemplated that the sensor 121 may be self-powered and not require a separate stored-energy power supply. For example, a piezoelectric transducer may be utilized as the acoustic transducer 122 such that signals detected by the transducer 122 also provide power to the sensor 121. In one embodiment, the piezoelectric transducer detects the signal and converts the detected signal into an electrical signal that is passively filtered and stored only if it satisfies the signal thresholds. Then, as in the current embodiment, the sensor 121 may utilize a passive RFID tag or other passive telemetry unit to communicate the tissue density data to an external device 200. Thus, in such embodiments, the sensor 121 functions without a dedicated or continuously draining power source. Further, the sensor 121 may utilize a piezoelectric and/or an electromagnetic power source that is not used as the acoustic transducer 122. In one embodiment, such a power source utilizes patient motion to create power for the sensor 121.

The sensor 121 may use the signal processor 126 and the memory unit 128 in combination with the acoustic transducer 122 to perform a type of comparative analysis to detect changes in the soft tissue of a joint. That is, an initial baseline or threshold range of acoustic signals will either be determined by the sensor 121 itself or provided to the sensor 121 by a caretaker. Then, the sensor 121 will subsequently monitor the acoustic signals emitted by the knee joint 102 and when the signals detected are outside of the baseline range of signals, the sensor 121 will store those signals or a data point representing the signals in its memory unit 128. This data can then be communicated to the caretaker. In some embodiments, the data is retrieved from the sensor 121 using the external device 200. Using the data obtained from the sensor 121, the caretaker may then choose an appropriate treatment plan for the patient. Further, the caretaker may choose to have the patient undergo additional examinations such as an MRI, a CT scan, or an x-ray. Based on the additional examinations and/or other factors, the caretaker may choose to adjust the threshold range in lieu of or in addition to choosing a treatment plan.

It is fully contemplated that a treating physician may want to change what the sensor considers the normal range of signals overtime. For example, as a soft tissue implant or graft is incorporated into the body the signals associated with soft tissue will change until the implant is fully integrated. Once the implant is fully integrated, the normal range of signals may be consistent for a period of months or years, but still may change over time requiring modification of the range. Thus, it is contemplated that the sensors of the present disclosure be programmable, self-learning, or both.

Self-learning implies that the sensor is able to determine the proper range of signals by monitoring the signals over a period of time and then via algorithms in its signal processing unit decide on the range of signals indicative of normal tissue density. In this regard, it is fully contemplated that the caretaker may be able to override the determinations made by the sensor by programming in the thresholds or, on the other hand, the caretaker may reset the sensor's determinations and simply have the sensor recalculate the proper range based on current signals detected. Thus, as described above when an implant becomes fully integrated the caretaker may decide to reset the self-learning sensor so that the ranges are based on the signals associated with the fully integrated implant.

In regards to setting the ranges, it is contemplated that the patient may be instructed through a series of movements. The series of movements will depend on the location and type of soft tissue being monitored. For example, where the soft tissue being monitored is the soft tissue of the knee, the movements may include sitting down, standing up, walking, climbing stairs, cycling, and/or other movements. Based on the sensed signals during the series of movements, the sensor threshold ranges may be set. Thus, instructing the patient through many of the normal motions and movements of everyday life may provide a good variety of signals that may be used to base the threshold signal range upon. Over time, the patient may again be put through a similar series of movements to reset or calibrate the sensor as seen fit by the caretaker.

Again, it is fully contemplated that the sensor 121 may be active or passive. Where the sensor 121 is active, the acoustic transducer 122 may be active and use a pulse-echo approach to monitor characteristics of the soft tissue. For example, in one embodiment, the sensor 121 utilizes ultrasonic waves in a pulse-echo manner to determine a density of the soft tissue. In such an embodiment, the transducer 122 emits a pulse signal into the soft tissue and receives a reflection of the pulse signal from the soft tissue. Based on the characteristics of the reflected signal, the density of the soft tissue can be determined. This density may be compared to a previously established baseline or a known value to detect any changes in the soft tissue and/or the need for medical treatment.

Utilizing sensors to monitor tissue characteristics has numerous applications in addition to those described above. For example, several applications of sensors are described in U.S. patent application Ser. No. 11/344,667 filed Feb. 1, 2006, which are hereby incorporated by reference in their entirety. Several methods of using sensors to monitor soft tissues according to the present disclosure will now be described. The methods described below are intended to be exemplary and should not be considered limiting. Numerous other methods of using the sensors to monitor soft tissue will be apparent to one skilled in the art based on the following.

Generally, the sensors of the present disclosure may be utilized to monitor changes in soft tissue. In that respect, the sensors may be utilized to monitor healing of the soft tissue, degradation of the soft tissue, and/or integration of the soft tissue. Thus, the sensors may be used in diagnosing, treating, and monitoring medical conditions. In that regard, the sensors may be used in pre-surgical applications, during a surgical procedure, and in post-surgical applications. For example, in some embodiments the sensors are configured for use in connection with surgical procedures such as ligament reconstruction, joint replacement, arthroscopy, meniscectomy, and other orthopedic surgical procedures.

Figure 4:
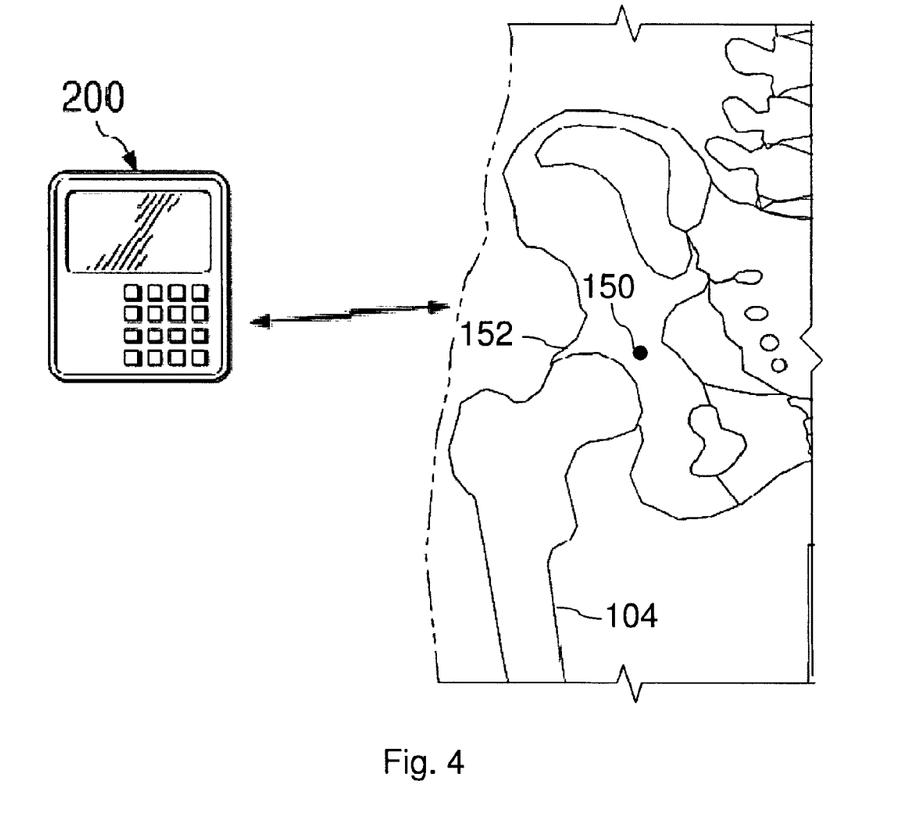
FIG. 4 is a partial front view of a sensor for monitoring soft tissue of a joint in use with a hip joint according to one embodiment of the present disclosure.
Figure 5:
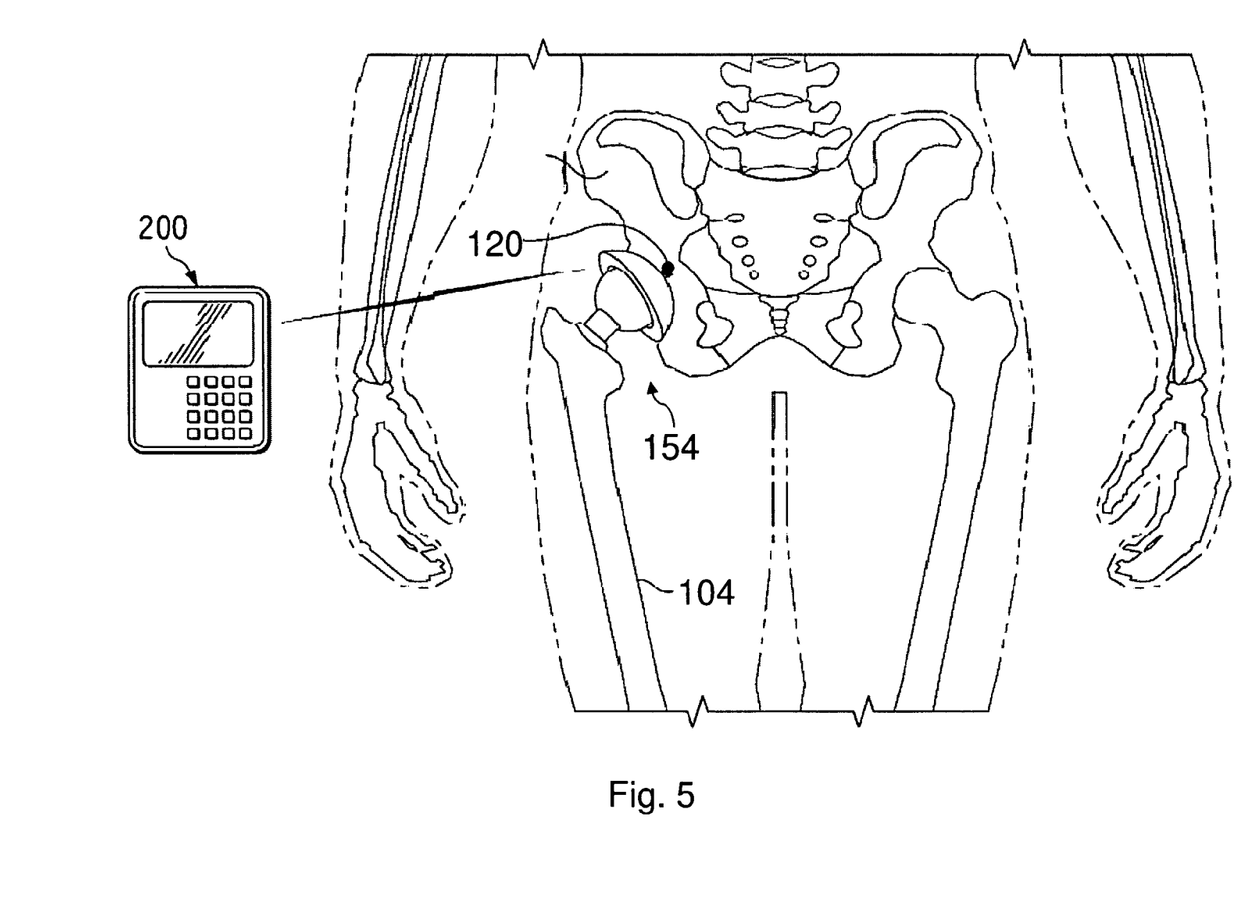
FIG. 5 a partial front view of a system including the sensor of FIG. 4 for monitoring soft tissue of a joint according to one embodiment of the present disclosure.

Referring now to FIGS. 4 and 5, shown therein is one embodiment of a sensor 150 for use in connection with a joint replacement surgery and, in particular, the implantation of a hip prosthesis. FIG. 4 is a partial front view of a patient with the sensor 150 positioned adjacent the hip joint. FIG. 5 is a partial front view of a patient with the sensor 150 positioned adjacent an artificial hip prosthesis 154. In the current embodiment, the sensor 150 is positioned within a portion of the acetabulum 152. The sensor 150 may be substantially similar to the sensors 120 and 121 described above. In that regard, although a single sensor 150 is shown in FIGS. 4 and 5, it is fully contemplated that additional sensors may be used to monitor the soft tissue of the hip joint. Thus, it is contemplated that the sensor 150 and any additional sensors may be placed in numerous positions and arrangements in and around the hip joint. For example and without limitation, the sensor(s) may be placed on or within portions of the acetabulum, femur, iliac crest, and/or pelvis. Further, in other embodiments, the sensor(s) may be positioned within muscle or other tissue adjacent the hip joint.

The sensor 150 may be programmable such that the function of sensor 150 may be modified according to the type of sensing desired. For example, in the current embodiment, the sensor 150 may be reprogrammed to monitor the hip prosthesis instead of the soft tissue after implantation of the hip prosthesis 154. In that regard, reprogramming the sensor 150 may comprise changing the threshold levels of the sensor 150 and/or may comprise changing the characteristic being monitored by the sensor 150. For example, in some embodiments, the sensor 150 may be reprogrammed to monitor wear, load, chemical presence, pH, temperature, motion, and/or other characteristics that may be associated with the prosthesis. In some embodiments, the sensor 150 may be reprogrammed wirelessly. In this manner, the sensor 150 may be reprogrammed in vivo without the need for an additional surgical procedure.

Figure 6:
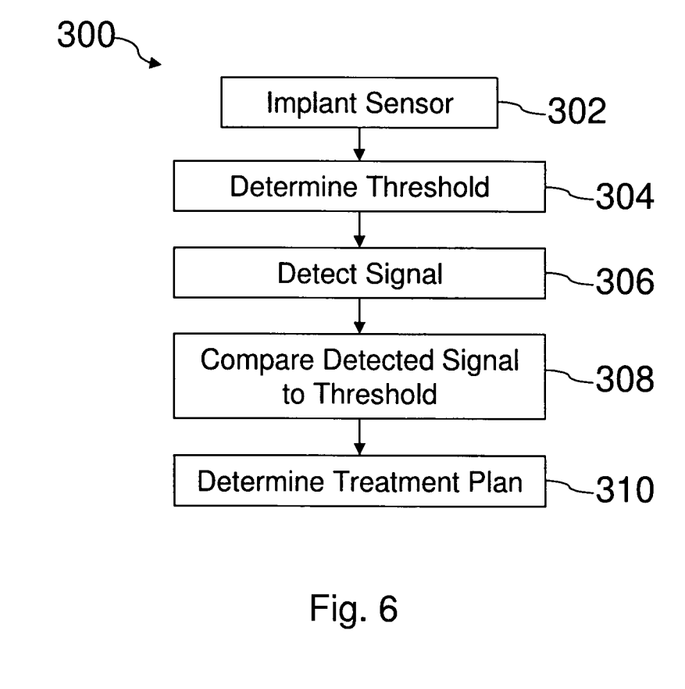
FIG. 6 is a flowchart illustrating a method according to one embodiment of the present disclosure.

Referring now to FIG. 6, shown therein is a flow chart representing a method 300 according to one embodiment of the present disclosure. The method 300 begins at step 302 with implanting a sensor. The sensor is implanted in the vicinity of a soft tissue to be monitored. In some embodiments, the soft tissue is the soft tissue of a joint. In some embodiments, the sensor is implanted into a portion of bone in proximity to the soft tissue. The sensor may be implanted using minimally invasive procedures. For example, in some embodiments the sensor is implanted transcutaneously via a catheter. In other embodiments, the sensor is implanted using an injection gun. Any suitable implantation technique may be used. Further, a plurality of sensors may be implanted.

The method continues at step 304 with determining a threshold or baseline measurement. This threshold is utilized to identify changes in the soft tissue and/or characterize the condition of the soft tissue. In some embodiments, the threshold is determined by utilizing the sensor to detect a signal associated with the soft tissue of a particular patient. In that regard, the signal may be obtained during movement of the joint connected with the soft tissue. In some embodiments, the patient is put through a series of movements to obtain the threshold measurement. In other embodiments, the threshold measurement is based on an established standard for signals associated with the soft tissue, rather than a reference signal from the actual patient. The value of the standardized signal may be affected by such things as the patient's age, weight, prior medical procedures, and/or other medical conditions.

The method 300 continues at step 306 with detecting a signal. The implanted sensor detects a signal associated with the soft tissue. In some embodiments, the signal is an acoustic signal. In other embodiments, the sensor monitors an impedance. The method 300 then continues at step 308 with comparing the detected signal to the threshold signal. Any changes in the detected signal relative to the threshold can be analyzed to determine if the change is indicative of soft tissue degradation, soft tissue healing, or other changes in the soft tissue. Thus, in one aspect of the current embodiment a difference between the detected signal and the threshold is indicative of soft tissue degradation. The magnitude of difference between the signals may be correlated to the degree of degradation, such that the greater the difference between the detected signal the greater the degradation of the soft tissue. The detected degree of degradation may be utilized to establish an appropriate treatment plan. If the soft tissue is degraded enough, joint replacement surgery or other medical treatment should be considered.

In some embodiments, the detected signal is compared the standardized threshold. The difference between the detected signal and the standardized threshold provides a relative indication of the health of the soft tissue compared to that standard. Thus, using the standardized threshold can provide an indication of the overall health of the soft tissue, while comparing the detected signal to a patient-specific threshold signal can provide information for determining whether the patient's condition is improving, getting worse, or staying the same. Thus, in some embodiments, these approaches are combined to provide a more complete analysis of the patient's condition.

The method 300 continues at step 310 with determining an appropriate treatment plan. The treatment plan is at least partially based on the detected differences between the detected signal and the threshold signal. In some instances, the treatment plan may include physical therapy, pharmaceuticals, surgical procedures, and/or other medical treatments. In some instances, the treatment plan includes total joint replacement. The appropriate treatment plan may be determined by a treating physician based on the detected signals.

Figure 7:
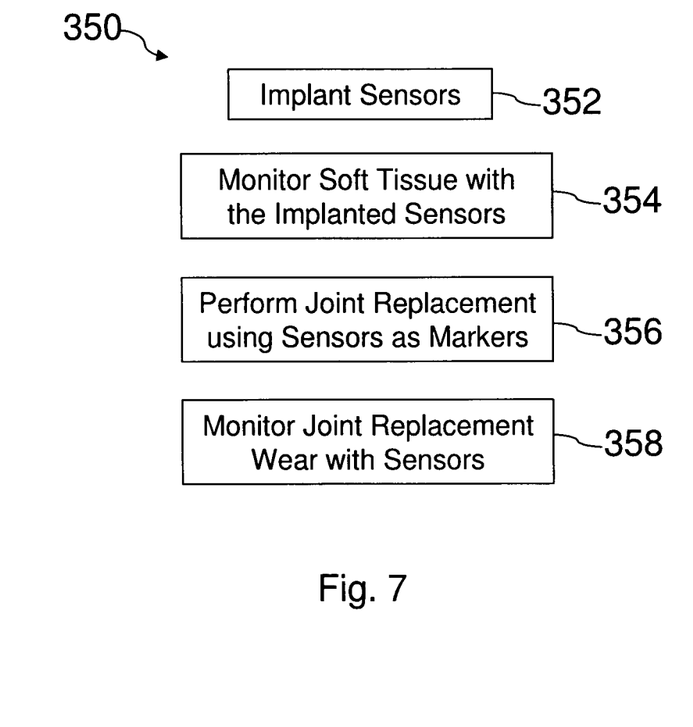
FIG. 7 is a flowchart illustrating a method according to one embodiment of the present disclosure.

Referring now to FIG. 7, shown therein is a flow chart representing a method 350 according to one embodiment of the present disclosure. In some aspects, the method 350 may be similar to the method 300 described above. The method 350 begins at step 352 with implanting sensors into a patient. In at least one embodiment, a plurality of sensors are implanted into the body such that sensors may provide positioning data. In that regard, the positioning data may include the position of the soft tissue; the position of lesions and/or holes in the soft tissue; anatomical positioning of bones and/or soft tissue; and/or other positioning data. In that regard, the sensors may be implanted such that the sensors can triangulate sensed signals and/or be used as fiducial markers for positioning information. The method 350 continues at step 354 with monitoring the soft tissue with the implanted sensors. Again, the sensors may detect changes in the soft tissue as previously described. In some embodiments, the sensors are further adapted to provide positioning data for the changes in the tissue. Thus, in some embodiments the treatment plan may be based at least partially on the location of the tissue changes.

The method 350 continues at step 356 with performing a joint replacement surgery. In some embodiments, a treatment plan is selected based on the data obtained from the implanted sensors. In the current embodiment, the treatment plan includes joint replacement surgery. In that regard, the implanted sensors may be utilized to assist in the surgery. In some embodiments, the sensors are utilized to provide positioning data for aligning and positioning the joint prosthesis. In some embodiments, the sensors are configured to communicate with a image guided surgery system. The image guided surgery system may then utilize the positioning data obtained from the sensors to properly implant the joint prosthesis. In that regard, in some embodiments the sensors act as fiducial markers. The sensors may be utilized to triangulate the position of the joint prosthesis relative to the sensors. In other embodiments, the sensors actively sense the position of the joint prosthesis and can provide the relevant 3-D positioning information to the image guided system and/or a surgeon.

The method 350 continues at step 358 with monitoring the joint prosthesis with the implanted sensors. In some embodiments, the implanted sensors are configured to monitor the wear, load, and/or other characteristic associated with the joint prosthesis. In that regard, the sensors may include a separate transducer configured for monitoring the characteristics of the joint prosthesis. In some embodiments, the sensors are programmable such that the sensors may be programmed to monitor the characteristics of the joint prosthesis after implantation. In yet other embodiments, at least some of the implanted sensors are configured for monitoring the characteristics of the joint prosthesis and soft tissue initially. The sensors can monitor the joint prosthesis for such potential problems as particle wear debris, misalignment, grinding, load-bearing, and/or other problems. The sensors may assist in early detection of the potential problems allowing early correction of the problem. In some instances, the sensors can prevent the need for a revision surgery.

While the methods 300 and 350 have been described with particular steps, it is fully contemplated that the methods may include additional or fewer steps. Further, it is fully contemplated that the order of the steps may be changed. It is also contemplated that one or more of the steps from each of the methods 300 and 350 may be combined. It is also contemplated that steps and methods of use apparent from the description of the sensors 120 and 121 may be incorporated into the methods 300 and 350.

In the context of the present disclosure, soft tissue is intended to include ligaments, tendons, cartilage, menisci, and other soft tissue of a joint. In some embodiments particular attention will be given to one or more of the specific types of soft tissue. However, this is not to be considered limiting. For example, as described above with respect to the knee joint 102 particular attention was given to the articular cartilage and menisci. In that regard, the system 100 has been described as being particularly configured to monitor changes in the articular cartilage and menisci. While the system 100 has been described in this manner, it is understood that the system 100 may be configured to monitor other soft tissue of the knee joint 102, including but not limited to the anterior cruciate ligament ("ACL"), medial collateral ligament ("MCL"), posterior cruciate ligament ("PCL"), lateral collateral ligament, and/or patellar tendon. Further, though the system 100 has been described with respect to the knee joint 102, the system may be used with other joints, such as a hip, an ankle, a shoulder, an elbow, a wrist, and/or other joint.

As mentioned above, it is contemplated that the sensors according to the present disclosure may utilize a variety of alternative techniques to power the sensor. For example, it is fully contemplated that the sensor may be piezoelectric. It is also contemplated that the sensor may simply use the kinematics of the body for power. Further, though the sensors described above have mostly been described as passive in the sense that they listen for indicators created by the body itself, it is also contemplated that the sensor may be powered such that it can send out a signal. Under such an approach, the sensor may utilize pulse-echo type sensing. The sensor would send out a signal and then listen for the echo. Based on the echo, the sensor could then detect changes in soft tissue. Similarly, instead of a pulse-echo system, a signal generator and a sensor could be utilized. The signal generator would send out a signal and the sensor would receive the signal and based on changes in the detected signals indicate changes in soft tissue. When detecting an emitted signal, either in pulse-echo or generator-sensor mode, it is contemplated that the signal may be acoustic, electric, or any other type of transmission that may be utilized to detect changes in tissue density.

In some embodiments, the sensors of the present disclosure may be accelerometers. An accelerometer can be utilized to detect vibrations related to the soft tissue. In some embodiments accelerometers and other sensing means may be used in combination. For example, accelerometer and an acoustic sensor may be used in combination. In that regard, it is contemplated that the vibrations detected by an accelerometer may be a result of acoustic emissions or the producing cause of the acoustic emissions. The accelerometer may be a single or multi-axis device. Also, a plurality of single-axis accelerometers—in the same or different axis—may be utilized to simulate the advantages found with a multi-axis accelerometer. For example, the use of a multi-axis accelerometer or a plurality of single-axis accelerometers may be used to produce vectored data to better differentiate between locations and types of soft tissue degradation.

An implantable sensor for detecting indicators of soft tissue wear of a joint is disclosed. The sensor comprises a sensing element for implantation into a portion of a bone adjacent the joint. The sensing element includes an external surface to maintain the sensing element in a fixed position within the bone and the sensing element is for detecting a signal indicative of a characteristic of the soft tissue of the joint. The sensor also comprises a telemetry circuit in communication with the sensing element adapted for transmitting a data set representative of the detected signal outside of the bone. The sensing element detects acoustic signals in some embodiments. The signal indicative of a characteristic of the soft tissue of the joint is an audible sound produced during movement of the joint in some embodiments. The signal indicative of a characteristic of the soft tissue of the joint is a vibration produced during movement of the joint in some embodiments. The implantable sensor is externally powered in some embodiments. The implantable sensor further comprises a power circuit for transferring power from an external device to the sensing element in some embodiments. The power circuit includes a coil for inductive coupling in some embodiments. The sensing element includes at least two sensors operable to determine an impedance between the at least two sensors in some embodiments, each of the at least two sensors having an outer surface for engaging a portion of a bone adjacent the joint and for maintaining each sensor in a fixed position within the bone. At least one of the at least two sensors is configured for placement in a distal portion of a femur adjacent a knee joint in some embodiments. At least one of the at least two sensors is configured for placement in a proximal portion of a tibia adjacent the knee joint in some embodiments. The sensing element is configured to serve as a reference marker in a joint replacement surgery in some embodiments. The sensing element is configured to interface with an image guided surgery system in some embodiments. The sensing element is further adaptable to monitor wear of an artificial joint in some embodiments. The implantable sensor is utilized in conjunction with a bone adjacent to a joint selected from the group consisting of an acetabulum, a pelvis, and a femur.

A system for detecting changes in joint cartilage is disclosed. The system comprises an implantable acoustic sensor for detecting an acoustic signal indicative of a characteristic of the joint cartilage and communicating a data set representative of the detected signal to an external receiver; and an external receiver in communication with the implantable acoustic sensor, the external receiver for receiving the data set representative of the detected signal from the implantable acoustic sensor. The implantable acoustic sensor is suitable for injection into a tissue adjacent the joint in some embodiments. The sensor is adapted for detecting sounds associated with joint motion in some embodiments. The sensor is adapted for detecting vibrations associated with joint motion in some embodiments. The sensor is externally powered in some embodiments. The external receiver is adapted for providing power to the sensor in some embodiments. The external receiver includes a signal processing unit for analyzing the data set communicated by the sensor in some embodiments. The external receiver includes a memory unit for storing the data set in some embodiments. The external receiver includes an output mechanism in some embodiments. The output mechanism is configured for outputting the data set in a human intelligible form in some embodiments. The human intelligible form is a visual display in some embodiments. The output mechanism is configured for sending the data set over a network in some embodiments. Communication between the sensor and the external receiver is wireless in some embodiments. The wireless communication is a RFID communication in some embodiments. The system further comprises a plurality of implantable acoustic sensors in some embodiments. The plurality of implantable acoustic sensors operate as redundancies in some embodiments. The plurality of implantable acoustic sensors operate together as an array in some embodiments. The sensor is adapted for percutaneous implantation in some embodiments. The sensor is substantially cylindrical in some embodiments. The sensor has a diameter less than 10 mm in some embodiments. The sensor has a diameter less than 4 mm in some embodiments.

A method of detecting soft tissue degradation in a joint is disclosed. The method comprises providing at least one acoustic sensor for detecting a signal indicative of a characteristic of the soft tissue of a joint, the at least one sensor having an external surface configured for implantation within a bone; implanting the at least one sensor into a bone adjacent the joint; operating the at least one sensor to detect a reference signal indicative of the characteristic of the soft tissue; operating the at least one sensor to detect a subsequent signal indicative of the characteristic of the soft tissue; and comparing the subsequent signal to the reference signal to detect changes in the characteristic of the soft tissue. The at least one sensor is implanted into a bone selected from the group consisting of a femur, a tibia, an acetabulum, and a pelvis in some embodiments. The at least one sensor is implanted into a portion of a bone selected from the group consisting of a distal portion of the femur and a proximal portion of the tibia in some embodiments. The method further comprises operating the at least one sensor to detect a plurality of subsequent signals indicative of the characteristic of the soft tissue; and comparing each of the plurality of subsequent signals to the reference signal to detect changes in the characteristic of the soft tissue in some embodiments. The method further comprises determining the detected changes in the characteristic of the soft tissue are indicative of soft tissue degradation; and performing a joint replacement procedure, including implanting an artificial joint in some embodiments. Performing the joint replacement procedure includes utilizing the at least one sensor as a reference marker in some embodiments. The at least one sensor is further configured to detect wear of the artificial joint in some embodiments. The method further comprises operating the at least one sensor to monitor wear of the artificial joint in some embodiments. Implanting the at least one sensor is performed percutaneously in some embodiments. Implanting the at least one sensor includes passing the sensor through a catheter in some embodiments.

A method comprises providing a plurality of implantable sensors for detecting signals indicative of a characteristic of cartilage of a joint; implanting each of the plurality of sensors into a bone adjacent the joint; operating the plurality of sensors to detect a reference signal indicative of the characteristic of the cartilage; operating the plurality of sensors to detect a subsequent signal indicative of the characteristic of the cartilage; and comparing the subsequent signal to the reference signal to detect any changes in the characteristic of the cartilage. The plurality of implantable sensors are configured for detecting impedance in some embodiments. The plurality of implantable sensors are paired such that each pair of sensors is capable of detecting an impedance indicative of the characteristic of the cartilage in some embodiments. The detected characteristic of the cartilage is a density in some embodiments. The method further comprises determining the detected changes in the characteristic of the cartilage are indicative of cartilage degradation; and performing a joint replacement procedure, including implanting an artificial joint in some embodiments. The joint replacement procedure is selected from the group consisting of knee replacement and hip replacement in some embodiments. The joint replacement procedure is performed using image guided surgery and the image guided surgery system utilizes the plurality of sensors as reference markers in some embodiments. The method further comprises operating the at least one sensor to monitor wear of the artificial joint in some embodiments. The plurality of implantable sensors are configured for detecting acoustic signals in some embodiments.

While the foregoing description has been made in reference to the knee and hip joints particularly, it is contemplated that the disclosed sensor may have further applications throughout the body. Specifically, such disclosed sensors may be useful to evaluate soft tissue and detect changes to soft tissue throughout the body. It is contemplated that the sensors may have particular application with respect to detecting changes in soft tissue of the joints. Further, the sensor may be applied to changes in soft tissue around fixation implants, joint implants, or any other type of implant. The sensors may also be applied to detect disc bulges or tears of the annulus when applied in the spinal region. Further, the sensor may be used in cooperation and/or communication with an implanted treatment device such as a pump or a stimulator. The pump or stimulator may be controlled based on the readings sensed by the sensor. These examples of potential uses for the sensor are for example only and in no way limit the ways in which the current disclosure may be utilized.

Further, while the foregoing description has often described the external device as the means for displaying sensor data in human intelligible form, it is fully contemplated that the sensor itself may include components designed to display the data in a human intelligible form. For example, it is fully contemplated that the sensor may include a portion disposed subdermally that emits a visible signal for certain applications. Under one approach, the sensor might display a visible signal when it detects indicators indicative of soft tissue degradation. The sensor might also emit an audible sound in response to such indicators. In this sense, the sensor might act as an alarm mechanism for not only detecting potential problems but also alerting the patient and doctor to the potential problems. This can facilitate the early detection of problems. Under another approach, the sensor might display a different color visible signal depending on the indicators detected. For example, but without limitation, in the case of measuring changes in soft tissue, the sensor might emit a greenish light if the signals detected by the sensor indicate that changes in the soft tissue is within the normal range, a yellowish light if in a borderline range, or a red light if in a problematic range.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A system for detecting indicators of soft tissue wear of a joint, comprising:
    an implantable sensor comprising:
        a sensing element adapted for implantation into a portion of a bone adjacent the joint, the sensing element having an external surface configured to maintain the sensing element in a fixed position within the bone, the sensing element configured to detect an acoustic signal indicative of a characteristic of the soft tissue of the joint; and
        a telemetry circuit in communication with the sensing element configured to transmit a data set representative of the detected acoustic signal outside of the bone, wherein at least a portion of the telemetry circuit includes a passive RFID tag so as to reduce the power requirements of the telemetry circuit; and
    an implantable accelerometer configured to detect a vibration signal indicative of a characteristic of the soft tissue of the joint, including an external surface configured to maintain the accelerometer in a fixed position within the bone and a telemetry circuit adapted for transmitting a data set representative of the detected vibration signal outside of the bone; and
    an external receiver in communication with the implantable sensor and the implantable accelerometer, the external receiver configured to receive the data sets representative of the acoustic signal and vibration signal and further configured to analyze the data sets to determine changes in the soft tissue;

wherein the accelerometer is one of a multi-axis accelerometer or a plurality of single-axis accelerometers to produce vectored data to differentiate between locations and types of soft tissue degradation, and wherein the at least one of the implantable sensing element and the implantable accelerometer are configured as a reference marker detectable by an image guided surgery system.

2. The system of claim 1, wherein the first signal is an audible sound produced during movement of the joint and the second signal is vibrations which result from the audible sound and vibrations produced during movement of the joint.

3. The system of claim 1, wherein the sensing element includes at least two sensors operable to determine an impedance between the at least two sensors, each of the at least two sensors having an outer surface for engaging a portion of a bone adjacent the joint and for maintaining each sensor in a fixed position within the bone.

4. The system of claim 3, wherein at least one of the at least two sensors is configured for placement in a distal portion of a femur adjacent a knee joint.

5. The system of claim 4, wherein at least one of the at least two sensors is configured for placement in a proximal portion of a tibia adjacent the knee joint.

6. The system of claim 1, wherein the sensing element is further adaptable to monitor wear of an artificial joint.

7. A system for detecting changes in joint cartilage, comprising:

an implantable acoustic sensor configured to detect an acoustic signal indicative of a characteristic of the joint cartilage, wherein the implantable acoustic sensor is adapted for injection into a tissue adjacent the joint;

a telemetry circuit in communication with the at least one implantable acoustic sensor configured to transmit a data set representative of the detected acoustic signal to an external receiver, wherein at least a portion of the telemetry circuit includes a passive RFID tag so as to reduce the power requirements of the telemetry circuit;

an implantable accelerometer configured to detect a vibration signal indicative of a characteristic of the joint cartilage and communicate a data set representative of the vibration signal to an external receiver, wherein the implantable accelerometer is adapted for injection into a tissue adjacent the joint; and an external receiver in communication with the telemetry circuit of the implantable acoustic sensor and the implantable accelerometer, the external receiver configured to receive the data sets representative of the detected acoustic signal and the detected vibration signal from the implantable acoustic sensor and the implantable accelerometer, the external receiver further configured to analyze the data sets to determined changes in the soft tissue;

wherein the accelerometer is one of a multi-axis accelerometer or a plurality of single-axis accelerometers configured to produce vectored data to differentiate between locations and types of soft tissue degradation, and wherein the at least one of the implantable sensing element and the implantable accelerometer are configured as a reference marker detectable by an image guided surgery system.

8. The system of claim 7, wherein the implantable acoustic sensor is adapted for detecting sounds associated with joint motion and the accelerometer is adapted for detecting vibrations which result from the sounds and vibrations associated with joint motion.

9. The system of claim 7, wherein the implantable acoustic sensor comprises a plurality of implantable acoustic sensors.

10. The system of claim 9, wherein the plurality of implantable acoustic sensors operate as redundancies.

11. The system of claim 9, wherein the plurality of implantable acoustic sensors operate together as an array.

12. The system of claim 7, wherein the implantable acoustic sensor is adapted for percutaneous implantation.

13. The system of claim 12, wherein the implantable acoustic sensor is substantially cylindrical.

14. The system of claim 13, wherein the implantable acoustic sensor has a diameter of less than 4 mm.

15. The system of claim 1, wherein the implantable sensor comprises a piezoelectric transducer such that acoustic signals detected by the piezoelectric transducer provide power to the implantable sensor.

* * * * *

UNITED STATES PATENT AND TRADEMARK OFFICE
CERTIFICATE OF CORRECTION

| | |
|---|---|
| PATENT NO. | : 8,915,866 B2 |
| APPLICATION NO. | : 12/016421 |
| DATED | : December 23, 2014 |
| INVENTOR(S) | : Nycz |

It is certified that error appears in the above-identified patent and that said Letters Patent is hereby corrected as shown below:

On the Title Page, Item (73), under "Assignee", in Column 1, Line 1, delete "Warsaw (IN)" and insert -- Warsaw, IN (US) --, therefor.

In the Specification

In Column 2, Line 63, delete "a partial" and insert -- is a partial --, therefor.

Signed and Sealed this
Fifth Day of May, 2015

Michelle K. Lee
*Director of the United States Patent and Trademark Office*